(12) United States Patent
Rude et al.

(10) Patent No.: US 10,788,683 B2
(45) Date of Patent: Sep. 29, 2020

(54) METHOD AND SYSTEM OF CREATING AN OPTIMIZED LENS FOR AN EYE

(71) Applicant: Loren Rude, Corona del Mar, CA (US)

(72) Inventors: Loren Rude, Corona del Mar, CA (US); Franklin W. Lusby, Solana Beach, CA (US)

(*) Notice: Subject to any disclaimer, the term of this patent is extended or adjusted under 35 U.S.C. 154(b) by 355 days.

(21) Appl. No.: 15/767,981

(22) PCT Filed: Oct. 7, 2016

(86) PCT No.: PCT/US2016/056116
§ 371 (c)(1),
(2) Date: Apr. 12, 2018

(87) PCT Pub. No.: WO2017/066101
PCT Pub. Date: Apr. 20, 2017

(65) Prior Publication Data
US 2018/0299695 A1   Oct. 18, 2018

Related U.S. Application Data

(60) Provisional application No. 62/240,453, filed on Oct. 12, 2015.

(51) Int. Cl.
| | |
|---|---|
| G02C 7/02 | (2006.01) |
| G02C 7/04 | (2006.01) |
| A61B 3/14 | (2006.01) |
| A61B 3/103 | (2006.01) |
| G05B 15/02 | (2006.01) |

(52) U.S. Cl.
CPC ............. *G02C 7/027* (2013.01); *A61B 3/103* (2013.01); *A61B 3/14* (2013.01); *G02C 7/04* (2013.01); *G05B 15/02* (2013.01); *G02C 7/047* (2013.01)

(58) Field of Classification Search
CPC .......... G02C 7/027; G02C 7/04; G02C 7/047; G02C 7/024; G02C 7/025; G02C 7/028; G02C 2202/22; A61B 3/14; A61B 3/103; G05B 15/02
USPC .................................................... 351/159.77
See application file for complete search history.

(56) References Cited

U.S. PATENT DOCUMENTS

| | | | | |
|---|---|---|---|---|
| 8,740,382 B1* | 6/2014 | Liu | ......... | A61B 3/113 351/210 |
| 2014/0078467 A1* | 3/2014 | Su | ......... | A61B 3/132 351/207 |

FOREIGN PATENT DOCUMENTS

WO    2013123044 A2    8/2013

* cited by examiner

*Primary Examiner* — William R Alexander
*Assistant Examiner* — Henry A Duong
(74) *Attorney, Agent, or Firm* — Troutman Pepper Hamilton Sanders LLP

(57) ABSTRACT

A method of creating an optimized lens for an eye including positioning a fitting lens onto the eye. The fitting lens may have one or a plurality of indicia. The eye and fitting lens using a computing device. A data set may then be produced, the data set defined by a three-dimensional relationship between the fitting lens and the eye. The computing device or a remotely connected computing device may then analyze the data set to generate one or more modifications to the fitting lens. The computing device or remotely connected computing device may then transmit the data set and the one or more modifications to a printing device to create the optimized lens for the eye.

20 Claims, 10 Drawing Sheets

Rays are focused on retina

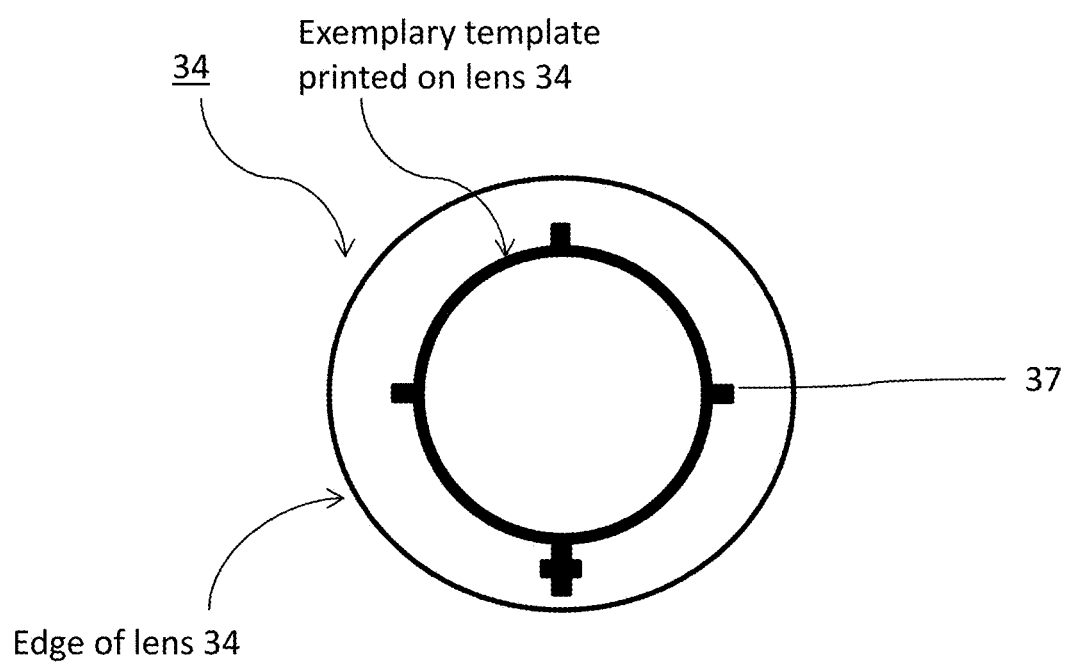

METHOD AND SYSTEM OF CREATING AN OPTIMIZED LENS FOR AN EYE

CROSS-REFERENCE TO RELATED APPLICATION

This Application is a United States national stage entry of an International Application Serial No. PCT/US2016/056116 filed Oct. 7, 2016, which claims priority to and benefit under 35 U.S.C § 119(e) of U.S. Provisional Patent Application Ser. No. 62/240,453, filed Oct. 12, 2015, the contents of which are hereby incorporated by reference in their entirety as if fully set forth below.

FIELD

This disclosure relates generally to improving the function of an eye and more particularly, towards improving methods and systems of aligning a lens with the visual axis of an eye.

BACKGROUND

The human eye works by receiving light rays from an object and focusing these light rays, by bending them. The two main focusing structures are the cornea, located in the anterior part of the eye, and the lens. It is understood that the retina is the primary light receiving element. In practice, light rays are received and bent by the cornea, then passed through the lens, and ultimately focused onto the retina. From the retina, the light rays become electrical impulses and are transmitted by the optic nerves to the brain.

The human eye may suffer from certain conditions or abnormalities. For example, an eye may experience "refractive errors" which are understood as any deviation from normal vision is referred to as a refractive error. Myopia, hyperopia, astigmatism and presbyopia are all understood as different types of refractive errors as explained more particularly below. With refractive error, light rays are focused at a point not on the retina, so that the image that is formed on the retina is blurry. Correcting refractive errors is therefore achieved by focusing the light clearly on the retina.

With respect to myopia, this condition is understood as nearsightedness, meaning, there is a mismatch between the length of the eye and the focusing power (curvature) of the cornea such that light rays are bent too much and therefore focused in front of the retina. The light rays continue on to the retina where they form a blurry image, resulting in difficulty seeing distant objects as clearly as near objects.

With respect to hyperopia, this condition is understood as farsightedness, meaning, there is a mismatch between the length of the eye and the focusing power (curvature) of the cornea such that light rays are not bent enough and therefore focused behind the retina. When light rays arrive at the retina they are not focused yet so they form a blurry image, resulting in difficulty seeing near objects as clearly as distant objects. Symptoms of hyperopia often do not show up until later in life because in youth, the up-close focusing mechanism can be used to bend the light rays more and thus make the vision clear. With aging, for example, the up-close focusing mechanism fatigues and the blurriness from hyperopia will then become apparent.

With respect to astigmatism, this usually results from the cornea being shaped more elliptical (e.g. such as part of a football) rather than spherical (e.g. such as part of a basketball), so that incoming light rays are focused at multiple points in the eye rather than on the retina; at the plane of the retina, the incoming light rays are almost all out of focus. Astigmatism is often combined with myopia or hyperopia.

Finally, the condition known as presbyopia is one that will ultimately affect everyone due to the loss of accommodation as a result of loss of lens flexibility that occurs with aging. With presbyopia, the vision up close becomes blurry and usually requires people age 40 and older to wear bifocals or reading glasses (or if they are a little nearsighted, take off their glasses and use their nearsightedness to read). Because vision correction surgery cannot reverse this aging process, presbyopia cannot be directly corrected surgically. However, there are surgical and non-surgical techniques available which can effectively reduce symptoms associated with presbyopia.

With respect to presbyopia specifically, as the average age of the human population has continued growing older in recent years with improving healthcare and living conditions, presbyopia has become increasingly prevalent. Presbyopia can be caused by defects in the focusing elements of the eye or, as a result of aging, the inability of the ciliary muscles to contract and relax to control the shape of the lens in the eye, or other possible mechanisms.

Typically, presbyopia is treated by reading glasses, which can be frustrating since reading glasses are known to be uncomfortable and costly both in monetary and convenience. Therefore, since current solutions in the art including contact lenses or other implants fail to efficiently and effectively treat presbyopia or may only resolve a single condition (see, e.g. laser vision correction such as LASIK), there exists a need to resolve these and other problems plaguing the art.

SUMMARY

The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In a preferred embodiment, a method of creating an optimized lens for an eye is disclosed, the eye having a visual axis and an optical axis with an angle kappa formed therebetween. The method may include the following steps: positioning a fitting lens onto the eye, the fitting lens having one or a plurality of indicia; scanning the eye and the fitting lens with a computing device; producing a data set defined by a three-dimensional relationship between the fitting lens and the eye; the computing device or a remotely connected computing device analyzing the data set to generate one or more modifications to the fitting lens; the computing device or remotely connected computing device transmitting the data set and the one or more modifications to a printing device to create the optimized lens for the eye.

The fitting lens may include an aperture with an annular shoulder region, and wherein the data set characterizes the eye and a center of the fitting lens in relation to the visual axis and pupil. The remotely connected computing device may be one or more locally or remotely located servers or computing devices. Furthermore, a local or remote network may be formed between the computing device and the one or more remotely connective devices.

It is understood that the computing device may be a mobile device, a smart phone, a tablet and/or any device with an optical system such as a digital camera. The optical system may include one or more light sources that are substantially coaxial and/or substantially non-coaxial with a projection axis of the light source or with an aperture of the optical system.

The scanning, producing and analyzing may preferably be defined by a set of instructions resident to the computing device or operatively coupled to the computing device via the remotely connected computing device. The scanning, producing and/or analyzing steps may be automatically executed by moving the computing device to a predetermined position relative to the eye or by moving the computing device in a predetermined manner.

Optionally, the scanning, producing and analyzing steps may also be manually actuated by the computing device receiving actuation input from a user. The actuation input may be capacitive input to a graphical user interface of the computing device, audible input received by a sensory input mechanism of the computing device (e.g. a microphone), may be caused by depressing a button on the computing device or a computing device operatively connected to the computing device, or caused by movement of the computing device in a predetermined manner.

The optical system (e.g. a digital camera) of the computing device may scan the eye by capturing and storing an image in a non-transitory computer readable storage medium of the computing device or the remotely connected computing device. The eye may be scanned and the data set may be produced by single-target fixation measuring, multi-target fixation measuring, and/or multi-fixation target measuring techniques.

The one or plurality of indicia of the fitting lens may include externally visible indicators as to alignment of the visual axis and pupil center of the eye relative to the fitting lens. In this respect, the indicia may be constructed from one or more markings or notches, and wherein the externally visible indicators include one or more rotational or centering relationships between the fitting lens and the eye.

The optimized lens may be individualized to an eye suffering from presbyopia or a contact lens for iris abnormalities, corneal scars, or irregular pupils. Accordingly, the optimized lens may be a contact lens, a design contact lens, a multifocal contact lens, or a cosmetic contact lens and include a prism ballast, double slab-off, or a rotation-protective mechanism. Furthermore, the fitting lens may be positioned anywhere on the eye including under a corneal flap of the eye.

Preferably, the printing device may print the optimized lens using the one or more modifications and data set such that the optimized lens can improve the prior effect of the fitting lens on the eye for any number of conditions including depth of focus relative to the fitting lens.

A system for creating an optimized lens for an eye is also disclosed, the system comprising a fitting lens operable to be positioned on the eye. A computing device is included in the system and is operable to scan the fitting lens and the eye and generate a data set defined by a three-dimensional relationship between the fitting lens and the eye. The computing device or a remotely connected computing device may be operable to analyze the data set and generate one or more modifications to the fitting lens. A printing device is comprised by the system and in communication with the computing device, the printing device operable to receive the data set and one or more modifications from the computing device to create the optimized lens for the eye.

The computing devices and the printing device may be directly or indirectly connected to each other such that the computing devices and the printing device may be in communication through one or more local or remote networks. The fitting lens may further comprise an aperture with an annular shoulder region, and wherein the data set may characterize the eye and a center of the fitting lens in relation to the visual axis and pupil. The remotely connected computing device may be one or more locally or remotely located servers or computing devices.

The computing device may scan the eye, generate the data set, and determine the one or more modifications by executing a set of instructions resident thereon or operatively coupled to the computing device via the remotely connected computing device. The instructions are automatically executed by moving the computing device to a predetermined position relative to the eye or by moving the computing device in a predetermined manner. Optionally, the computing device may be operable to receive actuation input from a user, wherein the instructions are manually actuated by the computing device receiving the actuation input.

The actuation input may be capacitive input to a graphical user interface of the computing device, audible input to a sensory input mechanism of or operatively coupled to the computing device, caused by depressing a button on the computing device or a computing device operatively connected to the computing device, or caused by movement of the computing device in a predetermined manner. An optical system of the computing device may be operable to scan the eye by capturing and storing an image in a non-transitory computer readable storage medium of the computing device or the one or more remotely connected computing device.

Preferably, the one or more indicia of the fitting lens are constructed from one or more markings or notches such that externally visible indicators of the fitting lens include one or more rotational or centering relationships between the fitting lens and the eye. An optimized lens may be prepared by any of the herein described processes.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

FIG. 15 depicts a close up of an exemplary fitting lens.

DETAILED DESCRIPTION

Figure 1:
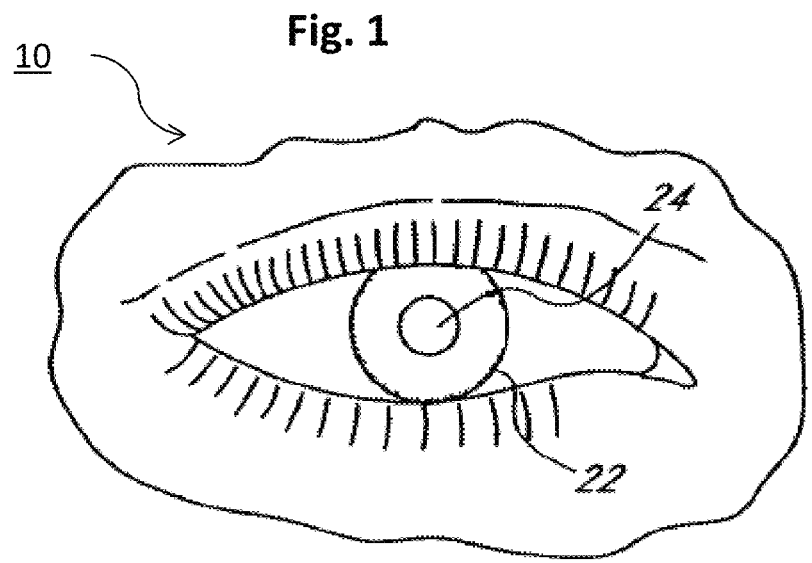
FIG. 1 is an exemplary view of a human eye.

Unless defined otherwise, all terms of art, notations and other scientific terms or terminology used herein have the same meaning as is commonly understood by one of ordinary skill in the art to which this disclosure belongs.

In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entirety. If a definition set forth in this section is contrary to or otherwise inconsistent with a definition set forth in the patents, application, published applications and other publications that are herein incorporated by reference, the definition set forth in this section prevails over the definition that is incorporated herein by reference.

As used herein, "a" or "an" means "at least one" or "one or more." As used herein, the term "user", "subject", "end-user" or the like is not limited to a specific entity or person. For example, the term "user" may refer to a person who uses the systems and methods described herein, and frequently may be a technician. However, this term is not limited to end users or technicians and thus encompasses a variety of persons who can use the disclosed systems and methods.

As used herein, it is understood that artificial lenses may be either intraocular or pseudophakic lenses that are implanted into the eye. Artificial lenses may also include contact lenses that are applied to, placed or assembled on or onto (hereinafter "assembled on") the eye or features of the eye (e.g. the cornea) and are relatively easy to remove from the eye.

The term "computing device" can mean any device that is programmable and/or capable of carrying out computation such as a mobile device, a smart phone or tablets and/or any device with an optical system with scanning capabilities.

The term "optical system" as it may be used with "computing device" may include a camera integrated with the computing device itself and/or directly or indirectly attached thereto that is designed to scan an image of particular object and render a set of data describing that object based on the image scan.

The term "remote connection" can mean any connection that is not direct such as wireless connection through radio waves such as wireless LAN, Bluetooth, WiMAX, WiMAX2, LTE, and/or HSDPA. Most contact lenses do not position themselves on the cornea. Certain features of the contact lens, for example, the optical center, do not line up precisely with certain features of the eye, for example, the visual axis. The herein described system produces an analysis of how a contact lens may fit a cornea so that certain optical or design features of the contact lens, for example, the optical center, can be positioned on the contact lens so that when the contact lens is fitted to the eye, those optical or design features will be positioned precisely with certain points on the eye, for example, the visual axis.

The system may comprise multiple contact lenses that position themselves on a given cornea the same way; a first lens being a template lens and imprinted with visible reference markings. The second lens may be individualized to ultimately be fitted to the cornea. In certain embodiments, the template lens may be placed on the cornea and an image of how it is positioned on the subject eye may be captured using a computing device. Using this information, it may be determined how the template markings are positioned with respect to certain features of the eye, such as the visual axis. With this data, the second contact lens can then be transformed and customized so that certain elements are positioned on the contact lens and thus ultimately on the eye, in a precise desired location.

The disclosed solution can now be better understood turning to the following detailed description. It is to be expressly understood that the illustrated embodiments are set forth as examples and not by way of limitations on the embodiments as ultimately defined in the claims. This herein disclosed solution may be directed towards optimizing the creation and assembling of ophthalmic implants and/or contact lenses to resolve certain conditions of the eye including presbyopia, and other herein discussed conditions, which affect depth of focus and/or other eye problems which may cause glare, halo and di- or poly-opia. Eye implants and contact lenses occasionally utilize what is known as pinhole vision treatment. In this respect, implants and contact lenses may be created and assembled with the eye as needed, including in communication with the cornea, implanted into the eye or as a corneal inlay.

With respect to patients suffering from presbyopia with healthy distance vision, such patients can be particularly difficult to treat under current approaches. This is because these patients may not wear glasses and/or don corrective contact lenses or other visionary spectacles. Such patients may also be hesitant to risk their otherwise healthy distance vision for an improvement to near vision in light of the herein acknowledged safety costs and unpredictable outcome that may result in additional surgery. Accordingly, there is a need to provide improved, safer, cost effective individualized treatment for patients with presbyopia and specifically those patients suffering from presbyopia with healthy distance vision.

Currently known methods generally assemble implants onto the patient's eye and then align the implant during implantation. The currently disclosed solution is designed to measure and define a relationship between a visual axis and a pupil center of a patient's eye with one or multiple fitting lenses with a plurality of indicia. The fitting lens may be customized to the patient initially or may be a template with indicia (e.g. one or more markings) to indicate to the end-user that fitting lens is properly aligned. The indicia may provide visual indicators as to how the one or more fitting lenses may have been positioned on the eye in relation to one or more features of the eye such as the pupil center and/or the visual axis. The indicia may therefore allow a practitioner such as a surgeon to readily and easily to determine whether or how the fitting lens may have been assembled with the eye and what modifications to the optimized lens may be necessary. For example, the indicia may indicate to the practitioner whether the fitting lens is de-centered or has rotated. Alignment of the fitting lens with the eye may then be specifically measured and analyzed as described more particularly below so that ultimately an improved, optimized, and individualized lens can be produced and assembled with the eye. It is understood that the fitting lens may be a contact lens or template lens that is detachably or fixedly attached to the eye of the patient.

The herein disclosed solution described in system 100 is particularly advantageous in optimizing and individualizing more effective and safer lenses for treating conditions such as presbyopia. System 100 is also particularly effective and safer when optimizing and individualizing WF design contact lenses, multifocal contact lenses, cosmetic contact lenses for cosmetic treatment including cosmetic treatment of iris abnormalities, corneal scars, irregular and/or asymmetric pupils, and the like. In a preferred embodiment, the fitting lens 34 may have a pinhole aperture 38 that can be used to improve the eye's depth of focus such as with presbyopia.

Figure 2:
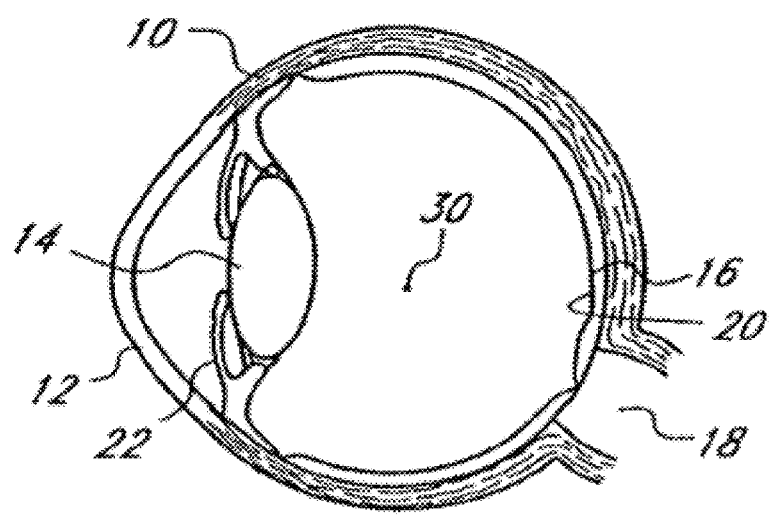
FIG. 2 is a horizontal cross-sectional view from above of the exemplary eye of FIG. 1.

Turning to the figures, FIG. 1 presents background information regarding an exemplary eye 10, wherein eye 10 is known to be situated in an eye-socket in the skull of a patient. FIG. 2 depicts a horizontal cross sectional view from above eye 10 of FIG. 1. Eye 10 rotates in a horizontal plane about center of rotation 30 and is shown with cornea 12 and phakic lens 14. Cornea 12 may be a first focusing element whereas lens 14 may be a second focusing element. Structurally, retina 16 typically lines the interior rear surface of eye 10 such that retina 16 is the portion of eye 10 that receives signals and transmits them to the brain by way of optic nerve 18. Iris 22 may also be provided with eye 10, iris 22 being defined by a layer of pigmented tissue and contains muscles that control the size of pupil 24. Entrance pupil 26 and single point 28 are seen as the image of iris 22 as viewed through cornea 12. Fovea 20 can also be seen being formed with retina 16, wherein fovea 20 is a portion of eye 10 that is particularly sensitive and may be offset from the axis of symmetry of eye 10.

Figure 3:
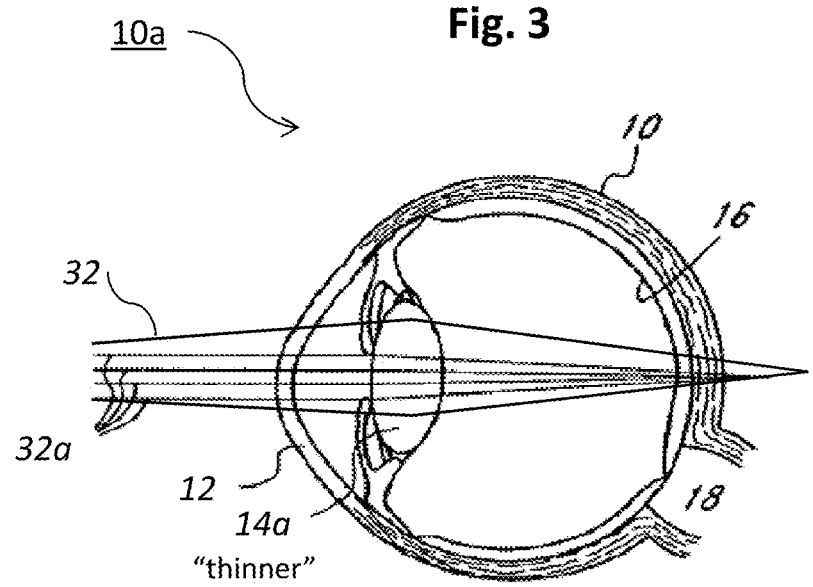
FIG. 3 is a horizontal cross-sectional view from above of an exemplary eye suffering from presbyopia, wherein the light rays can be seen meeting at a single point aft of the retina.

Moving to FIG. 3, light can be seen being transmitted through exemplary eye 10*a*. Eye 10*a* pertains to a patient who is suffering from presbyopia. This is observant through irregularities in phakic lens 14*a*, wherein rays 32 are seen passing through the cornea 12 and lens 14*a* and then refracted. Rays 32 can be seen in FIG. 3 failing to meet at a single focal point on retina 16 due to insufficient refraction (or bending). As is typical in presbyopia, rays 32 can be seen converging behind retina 16 resulting in vision that is disturbed and blurry. In FIG. 3, lens 14*a* is depicted relatively thin since this presbyopic eye 10 is unable to accommodate (i.e. enlarge or become fat). Accordingly, light rays 32 will not be bent to the extent they can be brought into focus on retina 16.

Figure 4:
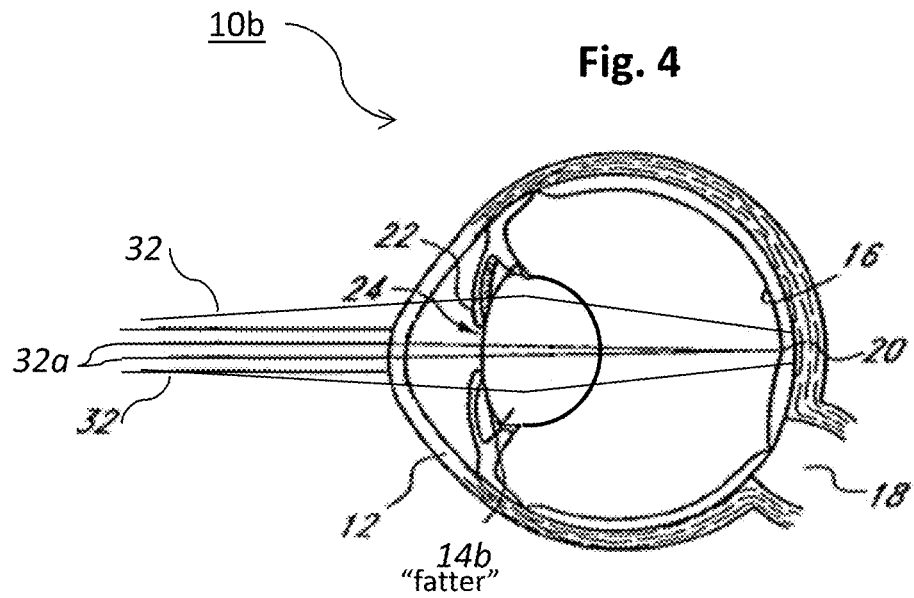
FIG. 4 is another horizontal cross-sectional view of an exemplary eye suffering from presbyopia, wherein the eye can be seen that the light rays meet at a single point on the retina (instead of aft).

By contrast, FIG. 4 depicts a non-presbyopic eye 10*b* (e.g., a young, pre-presbyopic eye) focusing on a near object (accommodating) where rays 32*a* are converging on a single focal point on retina 16. Lens 14*b* can be seen in FIG. 4 as being relatively enlarged or "fat" relative to lens 14*a*. Rays 32*a* extending from a distant object are parallel whereas rays 32 extending from a near object are divergent. For divergent rays 32 to be brought into focus, lens 14*b* has to add more focusing power (accommodate) to bend all of rays 32 and bring them into focus. In so doing, lens 14*b* becomes "fatter" or more spherical, as depicted.

Figure 5:
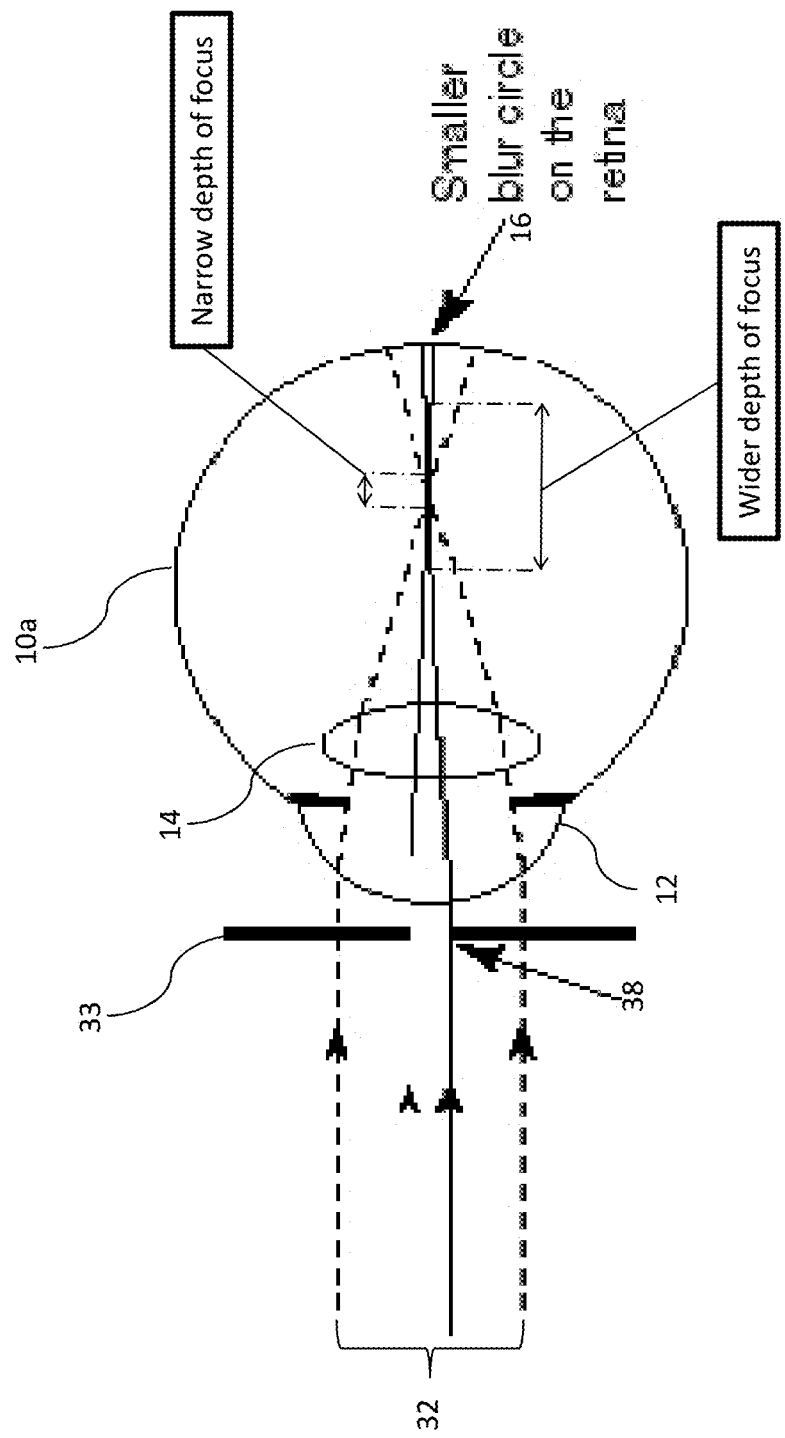
FIG. 5 is a horizontal cross-sectional view of an eye with an exemplary corneal inlay.

Current approaches to treat this blurry, disturbed vision of FIG. 3 include contact lenses and glasses to "pre-converge" light rays 32. However, this pre-convergence of rays 32 will cause distant objects to be blurry, which can be resolved with the above-described corneal inlays. See, for example FIG. 5, which depicts an exemplary pinhole aperture 33 with blacking most of the light rays 32 so that the resultant blur circle on retina 16 is relatively smaller. In this respect, it can be seen that aperture 33 results in a wider depth of focus as compared to without aperture 33 in which eye 10*a* has a narrower depth of focus. However, pinhole apertures such as 33 suffer from several conspicuous problems including heightened treatment expenses, a need for specialized equipment, limited efficacy, and increased safety risks. For example, corneal inlays that incorporate pinhole apertures 33, may be placed within the corneal stroma (tissue), which requires access to the inner layers of the cornea 12. Aperture 33 is then aligned with the visual and optical axes for a particular course of treatment. However, it may be difficult to know where exactly to place the aperture 33 to be sure it is positioned properly in the desired target location and/or to subsequently modify its location, if necessary.

Not surprisingly, this procedure has published targeted adverse event rates as per the FDA being less than 5% at 12 months. Furthermore, 3% of patients using the described corneal inlays ultimately have them surgically removed during pivotal trials and approximately 6% of patients during confirmatory trials. Stated differently, known current corneal inlay approaches have been shown as relatively unsafe and/or ineffective. Further, corneal inlays deemed ineffective or unsafe require follow-up removal or other surgical intervention techniques, thus putting a subject at further risk, increasing health care costs, and requiring more time by the subject being devoted to treatment.

The presently disclosed solution resolves these and other problems of the art by optimizing the efficacy of treatment and modifying an initial alignment relationship between a fitting lens and the patient's eye without a need for specialized equipment or surgical intervention. Instead, the herein disclosed solution may provide a temporary, fitting lens to be removably or detachably positioned on the eye of the patient to validate fit and/or alignment with eye 10 to in turn create an optimized, individualized lens particular to the patient's eye 10. In turn, treatment costs are diminished, safety is increased since the individualized lens does not require further surgical intervention after being assembled on the eye, and overall treatment efficacy for any number of conditions such as depth of vision along with a patient satisfaction that is appreciably higher.

Figure 6:
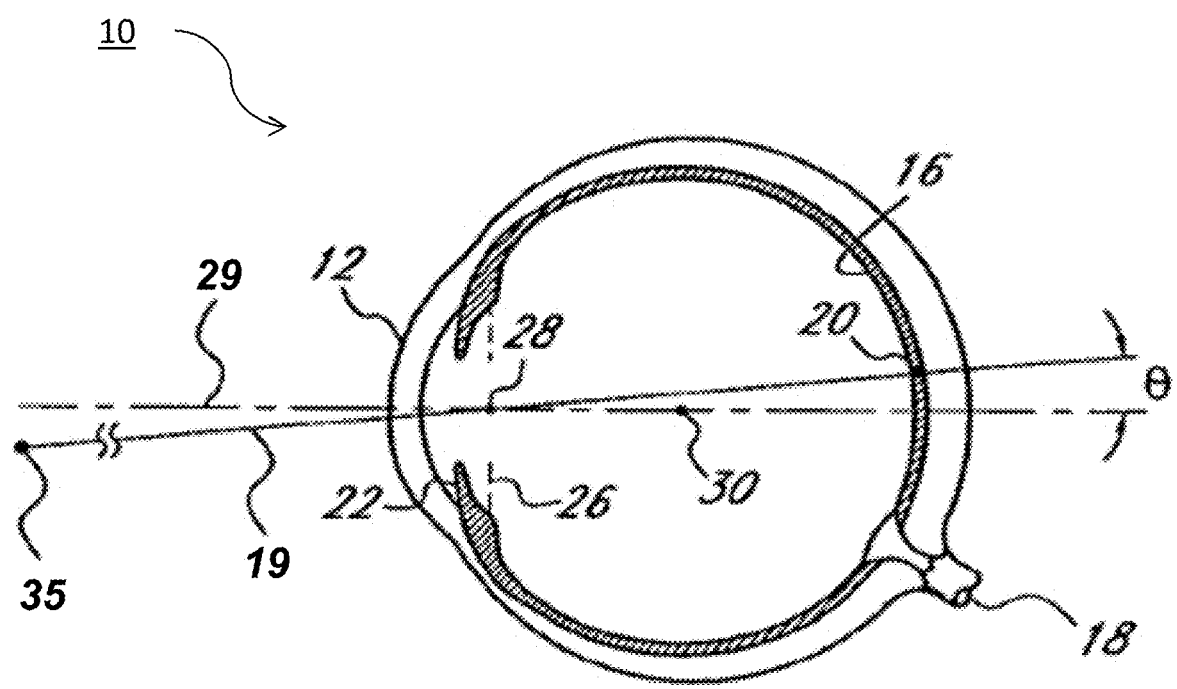
FIG. 6 is a horizontal cross-sectional view of the eye of FIG. 1 showing certain axes.

FIG. 6 depicts a horizontal cross-sectional view from above of eye 10 with visual axis 19 and eye 10's axis 29 of symmetry. Axis 19 as depicted connects fovea 20 and target 35. Axis 19 can be seen extending through a single point 28 of pupil 26. Axis 19 can also be seen corresponding to the central light ray 32*a* refracting from target 35 and passing through pupil 24 to fovea 20. As can be seen, axis 29 also passes through single point 28 and center of rotation 30 of eye 10. In practice, light is permitted to enter eye 10 through cornea 12 and iris 22 and is then focused by the cornea 12 and phakic lens 14. Eye 10 renders an image of target 35 at retina 16, wherein fovea 20, which is slightly off-set from axis 29 of the eye 10 so that axis 19 is oriented at an angle $\theta$ (e.g. approximately six degrees as per FIG. 6).

Figure 12:
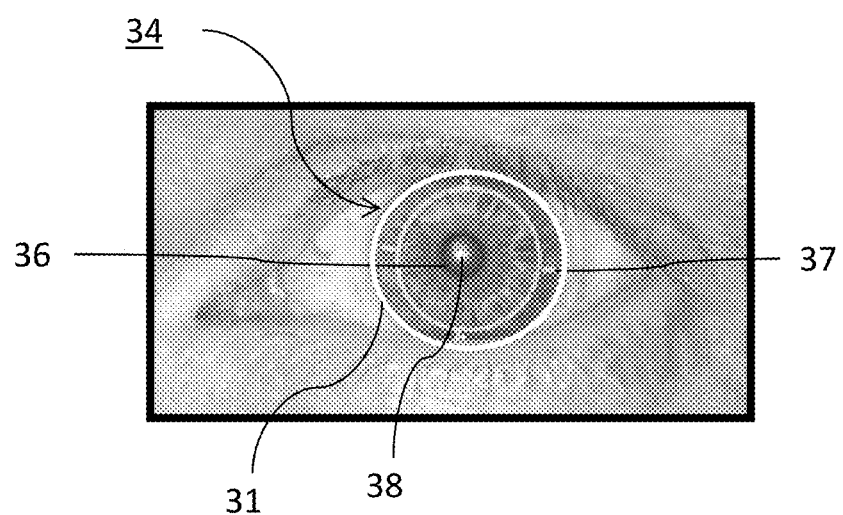
Figure 13:
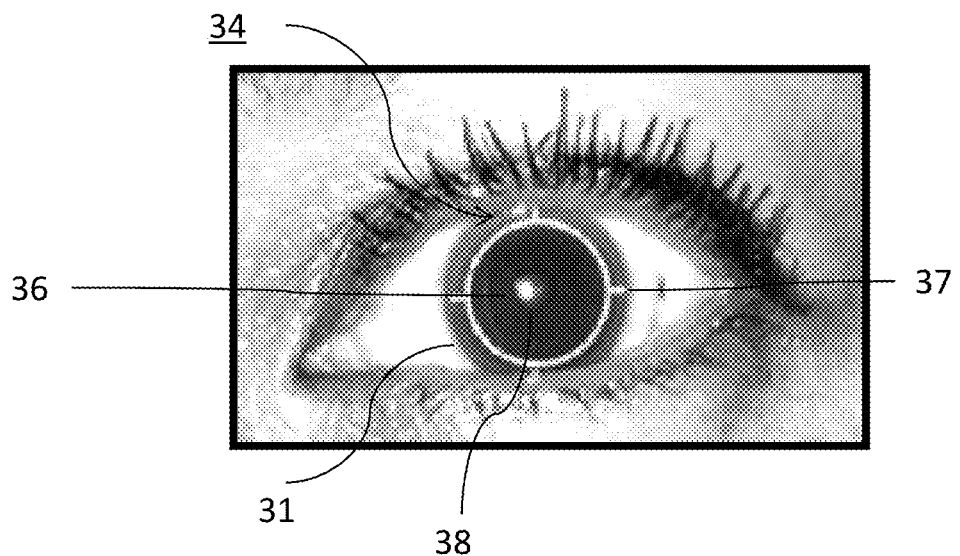
Figure 14:
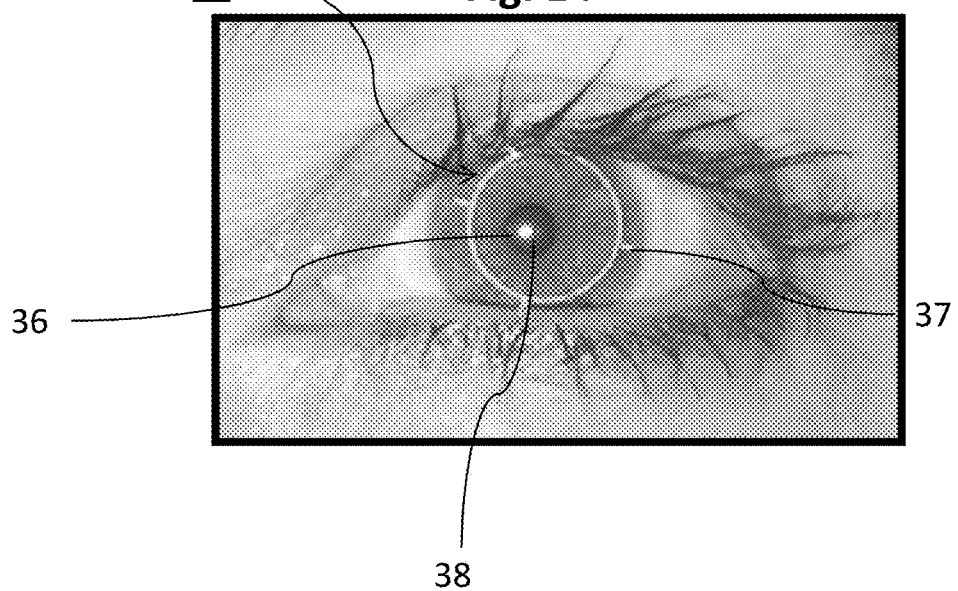

Referring now to treating an eye 10 with presbyopia, an exemplary, temporary fitting lens 34 may be assembled on eye 10 as seen in FIGS. 12-14. Lens 34 may be any cost-effective, easily manufacturable lens used to form a baseline of information to be discussed more particularly below with respect to relevant alignment, positional, and performance information of eye 10 with respect to lens 34 when assembled with each other. It can be seen in FIG. 7 that lens 34 may include aperture 38 in turn that may be designed to treat any condition including near distance and/or intermediate vision by focusing incoming light. Light rays 32 entering eye 10 are intended to pass through lens 34, cornea 12, and ultimately lens 14 so that rays 32 meet same as without aperture 38. Aperture 38 may include a smaller blur circle such that rays 32 contributing to the blurred image are blocked out. Placing an increasingly smaller aperture 38 in the proper location in the light path of an optical system can progressively increase depth of focus for eye 10. In practice, this effect actually occurs by blocking out peripheral, out-of-focus rays 32, and only admitting a smaller, central shaft of in-focus rays 32a. The image observed by the eye 10 in turn is seen more clearly as in FIG. 6.

To avoid rays 32 from meeting behind retina 16, rays 32 that are not capable of meeting on retina 16 are intended to be blocked by lens 34. While it is preferred that lens 34 cause all rays 32 to converge at fovea 20, in reality this is more difficult which is why temporary, fitting lens 34 is provided. Because of the costs and related complications of current approaches, lens 34 resolves certain problems in the art since it may be relatively inexpensive to produce, is easy to assemble with eye 10, and is readily measurable with respect to eye 10. In practice, where certain performance criteria of lens 34 is lacking, requires one or more precise modifications to better treat a particular eye 10, the herein disclosed system 100 renders such modifications possible without the need for specialized equipment or safety risk.

As can be seen in FIG. 7 and FIGS. 12-14, fitting lens 34 may be annular, rounded or circulate with aperture 38 centrally aligned. Lens 34 may have one or more set of indicia or markings 37 thereon visible by a surgeon or visible through a scan by a computing device 50 as described more particularly below. Lens 34 may also include edge 31 with a printed template pattern. Lens 34 may be temporarily, and through non-invasive means, assembled with cornea 12. Preferably, lens 34 may be smaller in thickness and surface area than a typical contact lens.

Figure 7:
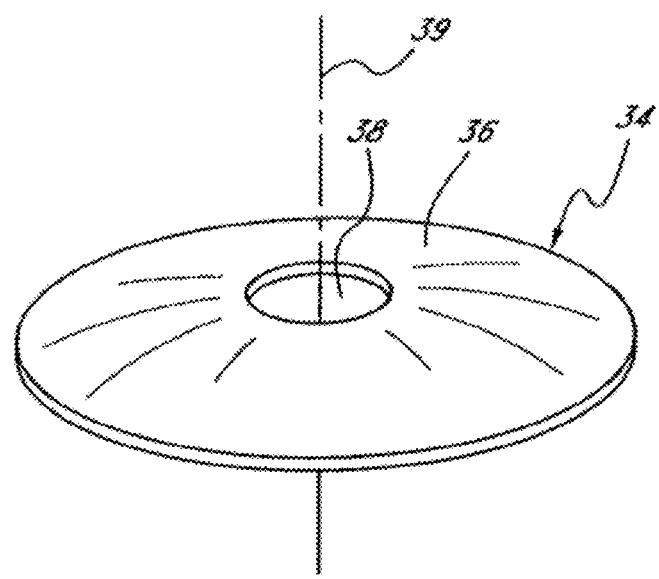
FIG. 7 depicts an exemplary lens to be used with the eye of FIGS. 4-5.

FIG. 7 specifically depicts a perspective view of fitting lens 34 with aperture 38 surrounded by annular shoulder 36 and one or more indicia indicating a particular position or alignment relative to eye 10. During assembly with eye 10, aperture 38 may be designed to be axially aligned with central axis 39. Shoulder 36 may be transparent or may be partially or completely opaque. In this respect, an opaque shoulder 36 may be operable to prevent light from being transmitted therethrough. While aperture 38 is depicted as being circular, the shape is not limited and can be any shape needed or desired. Optionally, aperture 38 may be shaped or in a pattern including one or more hexagons, octagons, ovals, pointed ovals, stars, rectangles or the like. While aperture 38 may be axially aligned with axis 39, aperture 38 may optionally be individualized to be off-center (e.g. not aligned with axis 39) depending on need or desire.

Figure 8:
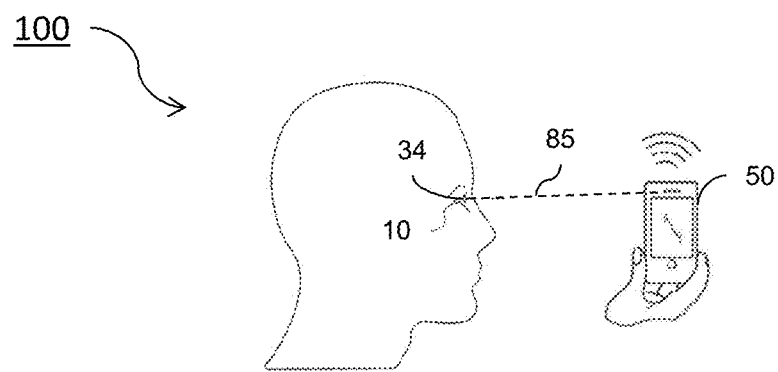
FIG. 8 depicts an exemplary system showing a fitting lens assembled on a patient being scanned by a computing device.
Figure 9:
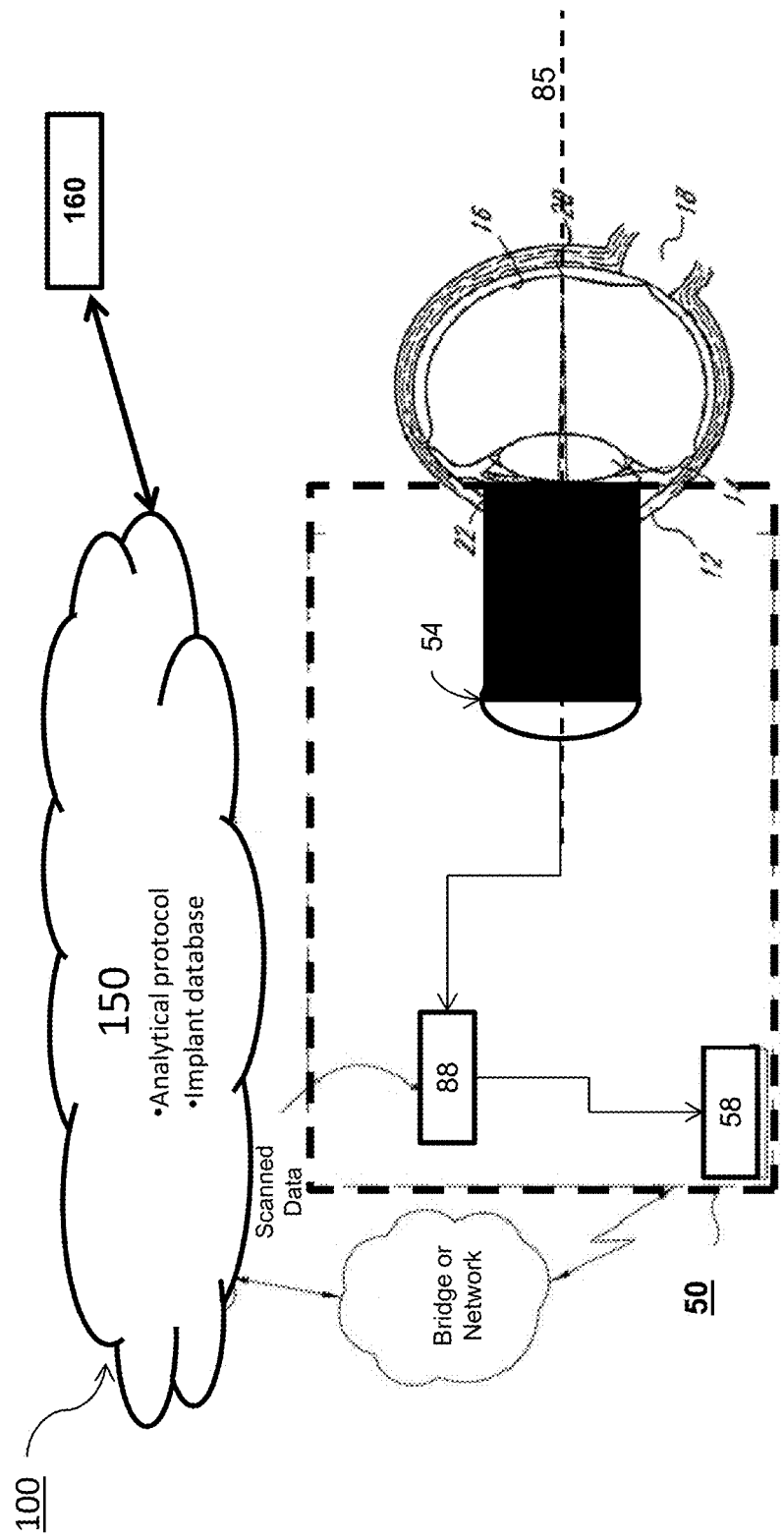
FIG. 9 depicts an expanded schematic overview of the system of FIG. 9.
Figure 10:
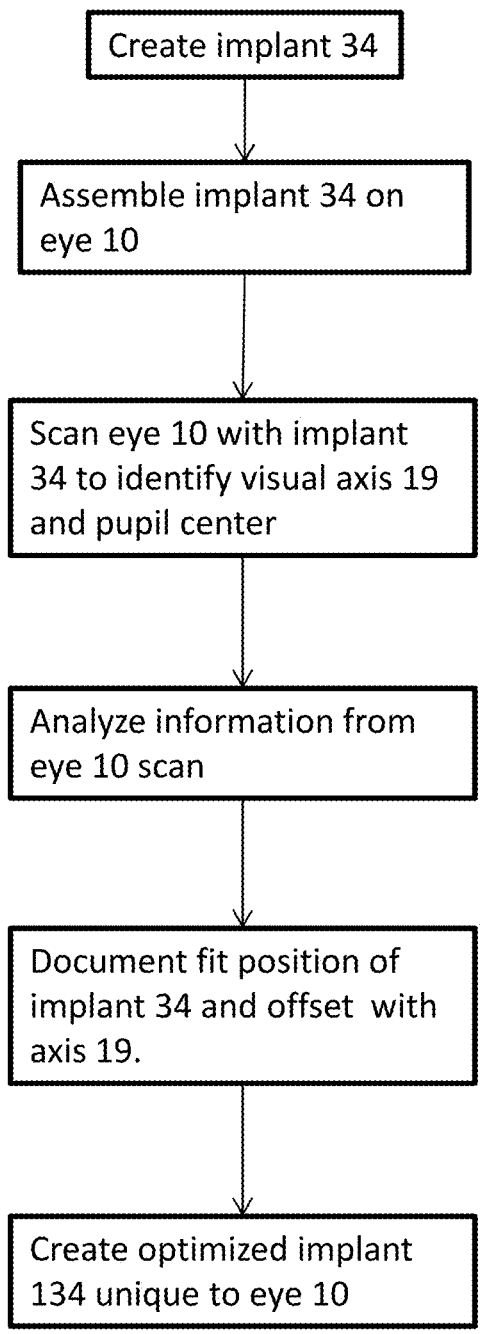
FIG. 10 is a flow diagram depicting one method of optimizing the efficacy of a lens on the patient.

FIGS. 8-10 depict a schematic overview of exemplary system 100 and method of individualizing eye treatment or eye care for a patient as described herein. Specifically, system 100 may be designed to develop and modify lens 34 into optimized lens 134 that takes into account how lens 34 positions itself on cornea 12 with respect to de-centration and/or rotation. As a result, optical elements can be positioned, manufactured, printed, and/or placed on lens 134 such that when lens 134 is applied to cornea 12, the optical elements will be centered on the visual axis 19.

Specifically, it can be seen that an exemplary computing device 50 may have a non-transitory computer readable storage medium and processor 58 operatively connected to optical system 54. Device 50 in turn may be directly or indirectly connected to an external server and/or external computing device 150 that in turn is in communication with printing device 160. It is noted that device 50 may utilize any number of communication protocols including internet protocol networks, multimedia subsystem networks, ethernet networks, or radio waves, wherein the communication protocol exchanges data between device 50 and one or more servers/devices 150. With respect to printing device 160, printing device 160 may be any known printer, method of manufacture that incorporates printing, or printing device 160 may involve some other manufacturing or fabrication process that does not incorporate "printing".

FIG. 8 specifically depicts an exemplary system 100 wherein eye 10 may be scanned by device 50 so that information 88 is then used in connection with various treatment and optimization methods described herein for locating and/or aligning lens 34 with eye 10 (e.g. Analyzing optimized alignment or positioning between lens 34 and visual axis 19). Information 88 may include a data set defined by coordinates in multiple dimensions including two- or three-dimensions, wherein the data set may include alignment and/or rotational information between lens 34 and eye 10. Device 50 can comprise optical system 54 that may include a camera with projection lens and visual imaging capabilities disposed internal to or on housing 52, optical system 54 optionally having specialized instructions, or being controlled by instructions resident to device 50 or in communication with device 50, to locate visual axis 19. For example, device 50 may be operable to simultaneously project one or a plurality of patterns or fixation targets for measuring and analyzing performance of lens 34 on eye 10.

Device 50 may be operable to provide a first reference target for eye 10. As seen in FIG. 8, a reference target may be capable of being imaged by a projection lens of optical system 54 of device 50 along projection axis 85. The reference target may be formed on and/or positioned at a first predetermined distance from eye 10. System 54 may comprise flash or a light source 56 for scanning and identifying axis 19, wherein source 56 may be integrally formed, detachable or modular with device 50.

In one embodiment, device 50 operatively connects to only one server/device 150 whereas in other embodiments, multiple independent server/devices 150 are in communication, directly or indirectly, with device 50. Each server/device 150 may communicate with device 50 via a local or remote network. Server/device 150 may be any device such as a personal computer, laptop, mobile computing device such as a smart phone or tablet, one or more servers and/or routers.

It is understood that the one or more networks formed between device 50 and the one or more server/devices 150 function as a communication bridge or conduit to establish a connection. Accordingly, the one or more networks may be a wireless network, a cellular network, a Digital Subscriber Line (DSL) network, a broadband cable access network, a Local Area Network (LAN), a Wireless Access Network (WAN), or a remote third party network. In turn, the one or more server/devices 150 can receive a data set from device 50 regarding eye 10 as to the spatial alignment and related fit of lens 34 thereon. Server/devices 150 are then operable to carry out a set of specialized instructions in accordance with a predetermined set of criteria associated with a particular condition such as presbyopia.

Specifically, optical system 54 of device 50 may be positioned in a predetermined position and/or alignment relative to eye 10, wherein optical system 54 may carry out a scan of eye 10 and lens 34. Optionally, system 54 of device 50 may be configured to automatically scan eye 10 and lens 34 once in position. Alternatively, system 54 may be executed by an end-user by an affirmative actuation such as depressing a button on device 50 or transmitting user input to device 50 that indicates to system 54 to carry out a scan. Such input may include capacitive input on a graphical user interface of device 50, auditory input from a sound recording device of device 50, or some predetermined change in gravity as measured by one or more accelerometers resident to device 50.

Scanning eye 10 and lens 34 in this respect may generate a set of data that describes quantitative spatial and alignment data 88. For example, data 88 may identify pupil 24 and/or visual axis 19 of eye 10 with respect to lens 34. This data may then be stored in a non-transitory storage medium of device 50 and/or analyzed locally by phone via processor 58 or transmitted to server/device 150. Feedback data 88 quantitatively describing performance, fit, alignment or the like of lens 34 is then analyzed and a set of processed data is then transmitted to printer 160 to manufacture an individualized lens 134. Preferably, lens 134 is an individualized contact lens or corneal inlay that is produced based on alignment and spatial relationships between eye 10 and lens 34.

Figure 11:
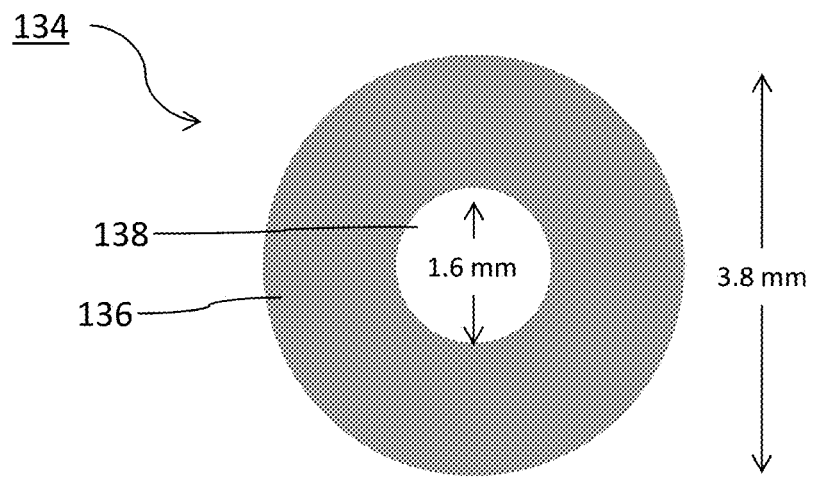
FIGS. 11-14 depict exemplary fitting lenses with indicia as assembled on an eye and ready to be scanned by a computing device.

As described more particularly below, (see, e.g., FIGS. 11 and 12), lens 34 may include indicia or markings and lens 134 may be optimized with information analyzed relative to the spatial relationship between eye 10 and lens 34 so that lens 134 can be effectively centered on visual axis 19. As described, the location of axis 139 on lens 134 is determined from how lens 34 fits or centers on eye 10. For example, the pinhole effect will be suboptimal unless lens 134 is centered on visual axis 19.

It is understood that an analysis of data 88 may be produced automatically or may require additional technical input from one skilled in the art such as a surgeon. For example, data 88 may be analyzed by device 50 or server/device 150 and this analyzed data may be transmitted to a surgeon for final input or approval of conclusions reached during analysis at server/device 150 and/or device 50 regarding information such as initial fit and/or alignment of lens 34, one or more proposed modifications to lens 34, or other diagnostic information related to eye 10. Data 88 may also prescribe specified alignment and/or positioning information of lens 134 on eye 10 for optimized fit and performance (e.g. positioning an optical center of lens 134 directly over visual axis 19).

Lens 134 may include features that are individualized for eye 10 including prism ballast, double slab-off, and other lens rotation protection features. It is contemplated that the one or more fitting lenses 34 of system 100 can include a spectrum of sizes and/or curvatures so that the end-user could choose one or a combination of features that optimizes stability when assembled on eye 10 for activities such as blinking. In this respect, in some embodiments after system 100 or end-user has determined the optimized fitting lens 34 of a plurality of fitting lenses 34 based on data 88 or the best fit as per indicia thereon, device 50 may then scan lens 34 as assembled on eye 10 to produce the foregoing data set 88 which may be a photograph, image or three dimensional map or set of coordinates describing eye 10 with respect to lens 34.

In a preferred embodiment, lens 134 may be a contact lens with an aperture 138 with an inner diameter of 1.6 mm and an annular region 136 surrounding aperture 138 with a diameter of 3.8 mm. Optionally, the annular region 136 may be substantially or partially opaque. Lens 134 in this embodiment may be designed to increase depth of focus of eye 10 to aid in activities such as reading. Using system 100 in this respect, one or more modifications to lens 34 is capable of being easily created, tested, and implemented for resultant, individualized lens 134. For example, aperture 138 may be centered on visual axis 19 and annular region 136 may be centered on pupil 24.

Advantageously, producing lens 134 with device 50 as described requires no special equipment. Instead, any number of devices 50 can be modified with a resident or remotely operated set of instructions (e.g. an "app" installed on device 50) to carry out the herein described steps and to scan and communicate the herein described information.

Device/server 150 may comprise a database of analytical instructions or information related to one or more patients. Database in this respect may be any type of electronic collection of data that is also well known in the art. System 100 depicted in FIGS. 8-10 can be expanded by including any number of devices/servers 150, printers 160, networks, network elements, and the like without altering the scope of the present solution.

It is also understood that system 100 may render accessible raw data 88 further described herein or any analyzed data therefrom to other remote or mobile locations. In turn, another surgeon, external device, or printing device may receive information associated with eye 10 and/or lenses 34/134 for further optimization or individualization of a patient's particular course of treatment.

Presently, it is common for consumers to have or have access to a smart phone with an optical system 54 such as a digital camera. System 54 may include one or more light sources that are substantially coaxial and/or substantially non-coaxial with axis 85 or with an aperture of system 54. Preferably, therefore, the herein disclosed system 100 and method of use is executed using device 50 as a smart phone by taking pictures using the optical system of a camera formed thereon. It is understood that data 88 may include one or more images of eye 10 and/or lens 34 captured using system 54 of device 50 using technologies such as charge coupled devices or complementary metal oxide silicon. Stated differently, system 54 of device 50 is a convenient, portable data scanner for eye 10 is readily available to any surgeon and/or patient. Optionally, data 88 may also be encrypted prior to transmission from device 50.

Once data 88 has been analyzed and information has been transmitted to printer 160 regarding individualized, improved lens 134, lens 134 may thereafter be assembled on eye 10 to improve the vision of a presbyopic patient as well as any other vision problems. By analyzing how lens 34 fits on eye 10, lens 134 can be made or customized so that its optical or design elements are precisely positioned so that when lens 134 is placed on eye 10, precise optical and/or design elements are in the precise position with respect to eye 10 and associated features (e.g. cornea 12). For example, lens 134 in the case of an aperture lens may be used therapeutically to optically correct presbyopia utilizing the pinhole effect. In other embodiments, lens 134 may be used as a testing or training aid for patients intending to have aperture inlay surgery since a significant amount of neuro-adaptation may be required after an inlay. This device would therefore allow this and other processes to occur before the actual surgery for inlay surgery.

More importantly, fitting lenses 34 can be made and assembled at relatively low cost and yet lead to optimized lens 134 for increased performance and safety without use of special equipment. In this respect, lens 134 improves appreciably upon lens 34 with regard to resolving vision issues stemming from irregularities and divots in cornea 12 or conditions such as macular degeneration by rendering alignment between lens 134 and eye more precise, for example, visual axis 19.

Preferably, an optical center of lens 134 may be designed to be positioned so that it matches visual axis 19 of eye 10. Various techniques can be used by system 100 to scan and analyze data 88 to define how lens 134 should differ with respect to lens 34. It is understood that angle kappa signifies the difference between pupil 24 and visual axis 19 of eye 10. It is understood that angle kappa may range between 0° or greater since the visual and optical axes can be aligned. With this in mind, if angle kappa appears to be altered by the presence of fitting lens 34, then system 100 and associated features may scan, measure, and calculate an offset between visual axis 19 of eye 10 without lens 34 (e.g. a contact lens) and an apparent visual axis 19' when lens 34 is assembled thereon.

Optionally, other methods may be used to analyze lens 34 as to its alignment and spatial relationship with eye 10 to define and produce lens 134, such methods including single-target fixation or multi-target fixation measuring methods. In this respect, eye 10 can be analyzed to determine if angular disparity between one or more target images when de-centering the eye. Eye 10 may be simultaneously fixated on the one or more targets if visual axis 19 is centered on the optical axis of the axis 85 of device 50. For example, when axis 19 is aligned with axis 85, the resultant image of eye 10 may be presumed fixated. If it is not, system 100 may produce an output that indicates how lens 134 may need to be modified based on analysis of data 88 associated with lens 34.

In other embodiments, a multi-fixation target technique may be used with the presently disclosed methods and devices to produce data 88 associated with eye 10 and lens 34. Specifically, multiple reticle patterns may be simultaneously projected from device 50 to eye 10 and lens 34 so as to create multiple targets, a first target at a short distance and a second or more targets at a greater distance than the first target. In this respect, eye 10 may be moved in a predetermined manner such laterally with respect to axis 39 of lens 34 until a predetermined angular displacement has occurred (e.g. a relatively low angular displacement) such that angular alignment between lens 34 and eye 10 can be readily determined and included in scanned data 88. In turned data 88 may then be used in system 100 to define and produce lens 134.

System 54 of device 50 may also include eye 10 locating module, said module being operable to automatically detect eye 10 from a predetermined distance once device 50 is positioned at the predetermined location relative to eye 10. This may be accomplished through various manners including external locating support mechanisms such as spacer with corresponding padding to be operatively connected with the area on the patient surrounding or adjacent to eye 10. The spacer may be mechanically attached to device 50 or may be operatively aligned and extend a predetermined distance between eye 10 and up to device 50. Whether using spacer and pad, device 50 may scan until locating eye 10 at a predetermined distance from the reference target of device 50. In turn, the patient may move and rotate eye 10 with lens 34 so that device locates axis 19 for scanning, measuring, and analyzing data 88.

Turning to FIG. 10, an exemplary process is shown utilizing the herein disclosed solution and system, the process being started with eye 10 of a patient receiving a first template lens 34, the lens 34 being preliminarily fitted for eye 10. Next, lens 34 is assembled on eye 10 wherein, device 50 is then obtained and/or positioned in a predetermined manner to scan eye 10 with lens 34 and identify certain spatial relationships, alignments, and landmarks of eye 10 including visual axis 19 as described above. The predetermined manner may be a predetermined alignment between visual axis 19 of eye 10 with device 50 and lens 34 and/or position of device 50 relative to eye 10 and lens 34. Device 50 then receives information from this scan and analyzes a data set 88 particular to lens 34 and its relationship with eye 10 so that positioning and any offset or alignment of lens 34 with respect to eye 10 is determined.

This information may then be analyzed, transmitted, and utilized to create an optimized lens 134 that takes into account the unique conditions of eye 10 and its relationship with lens 34 (e.g. alignment, orientation, and/or positioning of axis 19 and axis 39) so that preferably central axis 139 of lens 134 can be precisely aligned and positioned to resolve issues experienced by eye 10. The herein disclosed solution is not so limited, however, and lens 134 may be optimized and/or individualized based on other modifications separate from or in addition to central axis 139 as needed or required.

It is noted that data 88 may be analyzed by a skilled practitioner or may be analyzed by device 50 or device/server 150 remotely connected thereto. The information that is scanned and/or analyzed may be permanently stored in a non-transitory storage medium of device 50, of a remote computing device operatively connected thereto, and be directly or wirelessly communicated to a manufacturing device or other external display device.

In this respect, lens 134 may be individualized to be properly oriented with pupil 24 and curvature of lens 134 may be substantially aligned with curvature of cornea 12. Moreover, lens 134 may be held in place by any manner wherein vision of eye 10 and then be confirmed without invasive surgical means or other specialized, bulky equipment to verify fit and treatment efficacy. Instead, conveniently device 50 can be any size and moved with ease and efficiency while eye 10 remains stationary or is moved as instructed. Optionally, when a visual target of device 50 is aligned with eye 10 in a manner sufficient to properly scan and receive information 88 to analyze, a perceptible indication may be provided to the end-user. The indication may be one, or a combination, of sounds, images, vibrations or other perceptible sensory input. The indication may signify that device 50, eye 10, and lenses 34/134 are aligned.

Device 50 may further comprise a set of instructions resident to device 50 or remotely connected thereto with certain modules. The modules may include an image scan module, a lens marking module, or the like, to analyze relationships of axes 19, 29, 39, and 139. The lens marking module may be designed to scan lenses 34/134 assembled on eye 10 and generate an image to be analyzed by device 50. In turn, the image scan module in turn may be designed utilize system 54 of device 50 to produce an image of certain attributes of eye 10. These attributes may include locational relationship between axes 19, 29, 39, and 139 as well as other three dimensional relationships of features of lens 34 and eye 10.

Furthermore, control and/or system activation may be regulated by the end-user (e.g. doctor or surgeon), patient, a remote operator, or system 100 itself. For example, system 100 may be operable to automatically start a scan, image capture, marking, and/or analysis when at least one visual target of device 50 and axes 19, 29, and 39 upon in a predetermined arrangement or position by the end-user, the patient, or the like. In a preferred embodiment, a flash mechanism of system 54 and an associated camera lens of device 50 may be located at the same point (e.g. they are coaxial). The image captured by the camera lens may be precisely located on visual axis 19. In embodiments where device 50 is a smart phone, the flash mechanism of system 54 may be located some fixed distance from the associated camera lens. In this respect, the further away cornea 12 is from the camera of device 50, the less significant the error produced will be since the camera lens of device 50 and associated flash mechanism are not coaxial.

In contrast, if the error is significant (e.g., cornea 12 to camera of device 50 distance is small, thereby making the distance between the camera lens and the flash mechanism more significant), a correction can be calculated by system 100 to correctly place the captured image of the flash mechanism over visual axis 19 as long as the distance between the camera lens of device 50 and flash mechanism is known and eye 10 to camera lens of device 50 distance is known.

FIGS. 12-14 depict exemplary lenses 34 when assembled on different patient's eyes with exemplary apertures 38, annular shoulders 36, and indicia 37. The depictions of FIGS. 12-14 are merely examples and any number of indicia 37, apertures 38, or shoulders 36 may be included, modified, or removed as needed or required.

FIG. 15 depicts an exemplary lens 34 where it can be seen that an exemplary template has been positioned on lens 34, the exemplary template having indicia 37 disposed on lens 34 internal to the edge of lens 34. It is contemplated that lens 134 may be optimized so that features such as aperture 136 are disposed thereon for purposes of resolving issues such as presbyopia or as a test or training device prior to inlays.

The definitions of the words or elements of the following claims are, therefore, defined in this specification to not only include the combination of elements which are literally set forth. It is also contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination(s).

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what incorporates the essential idea of the embodiments.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of creating an optimized lens for an eye, the eye having a visual axis and an optical axis with an angle kappa formed therebetween, the method comprising:
    positioning a fitting lens on the eye, the fitting lens having one or a plurality of indicia;
    scanning the eye and the fitting lens positioned on the eye with a computing device;
    producing a data set defined by a three-dimensional relationship between the fitting lens and the eye;
    the computing device or a remotely connected computing device analyzing the data set to generate one or more modifications to the fitting lens; and
    the computing device or remotely connected computing device transmitting the data set and the one or more modifications to a printing device to create the optimized lens for the eye.

2. The method of claim 1, wherein the fitting lens further comprises an aperture with an annular shoulder region, and wherein the data set characterizes the eye and a center of the fitting lens in relation to the visual axis and pupil.

3. The method of claim 1, wherein the computing device is a mobile device, a smart phone, a tablet and/or any device with an optical system.

4. The method of claim 1, wherein scanning, producing and analyzing are defined by a set of instructions resident to the computing device or operatively coupled to the computing device via the remotely connected computing device,
    wherein scanning, producing and analyzing steps are manually or automatically executed by moving the computing device to a predetermined position relative to the eye or by moving the computing device in a predetermined manner.

5. The method of claim 1, wherein scanning, producing and analyzing are defined by a set of instructions resident to the computing device or operatively coupled to the computing device via the remotely connected computing device,
    wherein an optical system or camera of the computing device scans the eye by capturing and storing an image in a non-transitory computer readable storage medium of the computing device or the remotely connected computing device.

6. The method of claim 1, wherein scanning the eye and producing the data set is governed by single-target fixation measuring, multi-target fixation measuring, or multi-fixation target measuring techniques.

7. The method of claim 1, wherein the indicia of the fitting lens comprise externally visible indicators as to alignment of the visual axis and pupil center of the eye relative to the fitting lens, wherein the indicia are constructed from one or more markings or notches, and wherein the externally visible indicators include one or more rotational or centering relationships between the fitting lens and the eye.

8. The method of claim 1, wherein the fitting lens is a contact lens, and wherein the optimized lens is a contact lens, a design contact lens, a multifocal contact lens, or a cosmetic contact lens.

9. The method of claim 1, wherein the fitting lens is positioned under a corneal flap of the eye.

10. The method of claim 1, further comprising: the printing device printing on or printing the optimized lens using the one or more modifications and data set.

11. A system for creating an optimized lens for an eye, the eye having a visual axis and an optical axis with an angle kappa formed therebetween, the system comprising:
- a fitting lens operable to be positioned on the eye, the fitting lens having one or a plurality of indicia;
- a computing device operative to scan the fitting lens and the eye and generate a data set defined by a three-dimensional relationship between the fitting lens and the eye;
- wherein the computing device or a remotely connected computing device is operable to analyze the data set and generate one or more modifications to the fitting lens;
- a printing device in communication with the computing device, the printing device operable to receive the data set and one or more modifications from the computing device to create the optimized lens for the eye.

12. The system of claim 11, wherein the computing devices and the printing device are in communication through one or more local or remote networks, wherein the fitting lens further comprises an aperture with an annular shoulder region, and wherein the data set characterizes the eye and a center of the fitting lens in relation to the visual axis and pupil.

13. The system of claim 11, wherein the remotely connected computing device is one or more locally or remotely located servers or computing devices.

14. The system of claim 11, wherein the computing device scans the eye, generates the data set, and determines the one or more modifications by a set of instructions resident thereon or operatively coupled to the computing device via the remotely connected computing device.

15. The system of claim 14, wherein the computing device is operable to receive an actuation input from a user, wherein the instructions are manually actuated by the computing device receiving the actuation input,
Wherein the actuation input is capacitive input to a graphical user interface of the computing device, audible input to a sensory input mechanism of or operatively coupled to the computing device, caused by depressing a button on the computing device or a computing device operatively connected to the computing device, or caused by movement of the computing device in a predetermined manner.

16. The system of claim 14, the computing device further comprising an optical system, wherein the optical system is operable to scan the eye by capturing and storing an image in a non-transitory computer readable storage medium of the computing device or the remotely connected computing device.

17. The system of claim 11, wherein the optimized lens is individualized to the eye afflicted with presbyopia or related disorders, a contact lens for iris abnormalities, corneal scars, or irregular pupils.

18. An optimized lens for an eye having a visual axis and an optical axis with an angle kappa formed therebetween, the optimized lens prepared by a process comprising the steps of:
- positioning a fitting lens on the eye, the fitting lens having one or a plurality of indicia;
- scanning the eye and the fitting lens positioned on the eye with a computing device;
- producing a data set defined by a three-dimensional relationship between the fitting lens and the eye;
- the computing device or a remotely connected computing device analyzing the data set to generate one or more modifications to the fitting lens; and
- the computing device or remotely connected computing device transmitting the data set and the one or more modifications to a printing device to create the optimized lens for the eye.

19. The optimized lens of claim 18, wherein the fitting lens further comprises an aperture with an annular shoulder region, and wherein the data set characterizes the eye and a center of the fitting lens in relation to the visual axis and pupil; and
- wherein the indicia of the fitting lens comprise externally visible indicators as to alignment of the visual axis and pupil center of the eye relative to the fitting lens.

20. The optimized lens of claim 18, wherein the computing device comprises an optical system, wherein the optical system scans the eye by capturing and storing an image in a non-transitory computer readable storage medium of the computing device or the remotely connected computing device.

* * * * *